US00PP30571P2

(12) United States Plant Patent
Radler

(10) Patent No.: US PP30,571 P2
(45) Date of Patent: Jun. 18, 2019

(54) SHRUB ROSE PLANT NAMED 'RADMONYEL'

(50) Latin Name: *Rosa hybrida*
Varietal Denomination: RADMONYEL

(71) Applicant: The Conard-Pyle Company, West Grove, PA (US)

(72) Inventor: William J. Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/998,067

(22) Filed: Jun. 25, 2018

(51) Int. Cl.
*A01H 5/02* (2018.01)

(52) U.S. Cl.
USPC ..... Plt./104

(58) Field of Classification Search
USPC ..... Plt./104
See application file for complete search history.

*Primary Examiner* — Annette H Para
(74) *Attorney, Agent, or Firm* — Buchanan Ingersoll & Rooney PC

(57) ABSTRACT

A new and distinct variety of shrub rose plant herein referred to by its cultivar name, 'RADMONYEL', is provided which forms in abundance on a substantially continuous basis attractive, yellow colored blossoms. The vegetation is vigorous and the growth habit is very bushy and rounded. Attractive, semi-glossy, dark green foliage is formed. Very good disease resistance is exhibited. Additionally, the new variety is particularly well suited for growing as distinctive ornamentation in the landscape.

1 Drawing Sheet

Botanical/commercial classification:
Latin name—*Rosa hybrida.*
Common name—Shrub Rose Plant.
Varietal denomination: 'RADMONYEL'.

SUMMARY OF THE INVENTION

The new and distinct variety of *Rosa hybrida* shrub rose plant of the present invention was created by controlled breeding during July 2004 at Greenfield, Wis., U.S.A. by artificial pollination wherein two parents were crossed which previously had been studied in the hope that they would contribute the desired characteristics. The female parent (i.e., the seed parent) of the new variety was the 'Radmoon' variety (non-patented in the United States). The male parent (i.e., the pollen parent) of the new variety was the 'Radfrapeace' variety (non-patented in the United States).

The parentage can be summarized as follows:

'Radmoon' x 'Radfrapeace'

The seeds resulting from the above pollination were sown and small plants were obtained which were physically and biologically different from each other. Selective study resulted in the identification of a single plant of the new variety.

It was found that the new variety of shrub rose plant of the present invention possesses the following combination of characteristics:

(a) abundantly and substantially continuously forms attractive, yellow colored blossoms,
(b) exhibits a very bushy and rounded growth habit,
(c) forms vigorous vegetation,
(d) forms attractive ornamental semi-glossy, dark green foliage, and
(e) exhibits very good disease resistance.

The new variety well meets the needs of the horticultural industry and can be grown to advantage in the landscape, including parks, gardens, public areas, and residential landscapes, where attractive ornamentation is to be provided.

The new variety can be readily distinguished from its ancestors. More specifically, the 'Radmoon' variety (i.e., the seed parent) displays fewer petals than the new variety. Also the new variety displays a pure yellow and stable flower color, unlike the 'Radmoon' variety. Additionally, the 'Radfrapeace' variety (i.e., the pollen parent) displays a different flower color, lower petal count, more fragrance, and decreased petal substance compared to the new variety.

The new variety has been found to undergo asexual propagation in Cochranville, Pa., U.S.A. by a number of routes, such as vegetative cuttings. Asexual propagation, such as vegetative cuttings has shown that the characteristics of the new variety are homogeneous and stable and are strictly transmissible by asexual propagation from one generation to another. Accordingly, the new variety undergoes asexual propagation in a true-to-type manner.

The new variety has been named 'RADMONYEL'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plant of the new variety was approximately two years of age and was observed during May 2018 while growing outdoors on its own roots in Cochranville, Pa., U.S.A.

FIG. 1—illustrates a specimen of a plant displaying blossoms.

DETAILED BOTANICAL DESCRIPTION

The chart used in the identification of the colors is that of The Royal Horticultural Society ("R.H.S.") (R.H.S. Colour Chart, 2015 Edition). The description is based on the observation of a two years old specimen during May while growing outdoors on their own roots at Cochranville, Pa., U.S.A.

Class: Shrub Rose.

Plant:

*Growth habit*.—Very bushy and rounded.

*Vegetation*.—Vigorous.

*Foliage*.—Attractive semi-glossy, dark green.

*Blossoms*.—Attractive, yellow colored.

*Height*.—Approximately 50.0 cm on average.

*Width*.—Approximately 50.0 cm on average.

Branches:

*Color*.—Commonly a blend of near Yellow-Green Group 144A and near Greyed-Red Group 178B on old wood and commonly near Yellow-Green Group 144A on young stems.

*Length*.—Main stems are approximately 30.0 cm on average and secondary stems are approximately 15.0 cm on average.

*Thorns*.—Young thorns: color is commonly near Greyed-Purple Group 183D, length is approximately 5.0 mm on average, and width at point of attachment is approximately 3.0 mm on average. Old thorns: color is commonly near Greyed-Red Group 182B, length is approximately 1.0 cm on average, and width at point of attachments is approximately 5.0 mm on average.

Foliage:

*Young foliage*.—Color: upper surface is commonly near Purple Group N77A and under surface is commonly near Greyed-Purple Group 183A.

*Old foliage*.—Color: upper surface is commonly near Yellow-Green Group 147A and under surface is commonly near Yellow-Green Group 147B with the midrib and veins near Greyed-Orange Group 176A.

*Leaf margin*.—Serrate.

Leaflets:

*Number*.—Commonly 3, 5, and 7.

*Shape*.—Ovate.

*Texture*.—Upper surface: smooth. Under surface: smooth.

*Size*.—Terminal leaflet length is approximately 6.0 cm on average and width is approximately 4.0 cm on average. Lower leaflets: length is approximately 4.5 cm on average and width is approximately 3.3 cm on average. 5-leaflet leaf: length is approximately 13.0 cm on average and width is approximately 10.0 cm on average.

*Petiole*.—Texture: upper surface is smooth and under surface is glandular with some small prickles. Color: upper surface is commonly near Greyed-Orange Group 176A and under surface is commonly near Greyed-Orange Group 176B.

*Rachis*.—Color: upper surface is commonly near Greyed-Orange Group 176A and under surface is commonly near Greyed-Orange Group 176B.

*Stipules*.—Size: length is approximately 20.0 mm on average and width is approximately 7.0 mm on average. Margin: entire to erose. Color: upper surface is commonly near Green Group 137C with some mixing of Greyed-Orange Group 176A particularly close to the innermost portion and lower surface is commonly near Green Group 137D.

Inflorescence:

*Number of flowers*.—Commonly approximately 15-20 blooms on average on a single plant at once.

*Number of blooms per stem or in a cluster*.—Commonly 1 bloom per stem and can have up to 3 per cluster on average.

*Peduncle*.—Color: commonly near Yellow-Green Group 144B. Size: diameter is approximately 3.0 mm on average and length is approximately 3.5 cm on average. Surface texture: commonly sparsely covered in short, flexible thorns that measure approximately less than 2 mm on average in length.

*Sepals*.—Number: commonly 5. Upper surface: color is commonly near Green Group 143C and is covered in short pubescence. Under surface: color is commonly near Yellow-Green Group 144A and texture is puberulent. Size: length is approximately 3.0 cm on average and width is approximately 1.0 cm on average. Margin: entire with occasional extensions on two or three sepals measuring approximately 1.0 cm in length on average and approximately 1.0 mm in width on average.

*Bud*.—Shape: ovoid. Size: approximately 2.5 cm on average in length and approximately 2.0 cm on average in width. Color (when opening): commonly near Yellow Group 12A.

*Flower*.—Form: semi-double, cuplike. Size: diameter is approximately 8.0 cm on average and height is approximately 3.0 cm on average. Duration: flowers are commonly on the plant approximately 5 days. Color (when opening begins) upper surface is commonly near Yellow Group 12A and under surface is commonly near Yellow Group 12B. Color (at end of blooming): upper and under surfaces are commonly near Yellow Group 11D. Fragrance: very light and sweet. Number of petals: approximately 10 on average. Petal drop: excellent. Petal size: length is approximately 4.0 cm on average and width is approximately 3.8 cm on average. Petal shape: overall broadly obovate with a obtuse to crenate apex and mostly rounded base. Petal margin: entire. Petaloids: Number: commonly 5 per flower on average. Color: upper surface is commonly near Yellow Group 12A and under surface is commonly near Yellow Group 12B. Size: length is approximately 2.5 cm on average and the width is approximately 2.0 cm on average. Texture: smooth. Margins: variable, entire to erose. Shape: overall variable, oblong and mostly curving inward, round apex, and cuneate base. Stamen: number is approximately 107 on average. Anthers: number is approximately 107 on average and color is commonly near Yellow-Orange Group 22A with a thin margin near Greyed-Orange Group 163A. Filaments: length is approximately 1.0 cm on average and color is commonly near Yellow-Orange Group 17B. Pistils: arrangement is separate and free, and number is approximately 40 on average. Style: color is commonly near Yellow Group 2D and length is approximately 6.0 mm on average. Stigma: color is commonly near Yellow Group 3B and diameter is commonly less than 1.0 mm on average.

*Receptacle*.—Achenes: stand on the bottom and wall. Size: approximately 5.0 mm in diameter. Shape: round. Color: commonly near Yellow-Green Group 144A. Surface texture: smooth.

*Pollen*.—Color: commonly near Greyed-Yellow Group 162A. Amount: moderate.

*Hips/seed*.—None observed.

Development:

*Vegetation*.—Dark green, vigorous, and strong.

*Blooming*.—Abundant and substantially continuous from spring through frost.

*Resistance to diseases*.—Very good resistance for black spot, rust, and mildews.

The new 'RADMONYEL' variety has not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and substantially continuously forms attractive, yellow colored blossoms, (b) exhibits a very bushy and rounded growth habit, (c) forms vigorous vegetation, (d) forms attractive ornamental semi-glossy, dark green foliage, and (e) exhibits very good disease resistance;

substantially as herein shown and described.

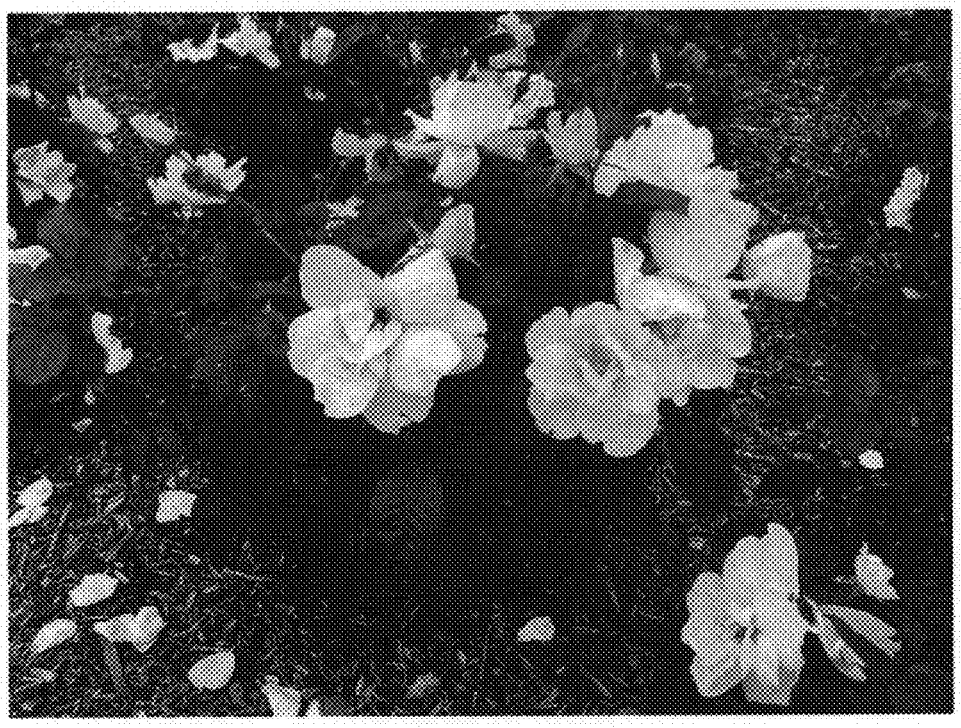

* * * * *